(12) United States Patent
Arcia et al.

(10) Patent No.: US 7,048,747 B2
(45) Date of Patent: May 23, 2006

(54) DEVICE AND METHOD FOR PERFORMING END-TO-SIDE ANASTOMOSIS

(75) Inventors: Rovil P. Arcia, Daly City, CA (US); Sam Lichtenstein, Vancouver (CA); Douglas Mehl, Redwood City, CA (US)

(73) Assignee: abbott Laboratories, Abbott Park, IL (US)

( * ) Notice: Subject to any disclaimer, the term of this patent is extended or adjusted under 35 U.S.C. 154(b) by 93 days.

(21) Appl. No.: 09/988,541

(22) Filed: Nov. 20, 2001

(65) Prior Publication Data

US 2002/0077636 A1  Jun. 20, 2002

Related U.S. Application Data

(62) Division of application No. 09/395,901, filed on Sep. 14, 1999, now Pat. No. 6,358,258.

(51) Int. Cl.
*A61B 17/04* (2006.01)
(52) U.S. Cl. .................. 606/139; 606/148; 606/153
(58) Field of Classification Search ............... 606/153, 606/144, 148, 149, 139
See application file for complete search history.

(56) References Cited

U.S. PATENT DOCUMENTS

| 312,408 A | 2/1885 | Hagen |
| 659,422 A | 10/1900 | Shidler |
| 2,127,903 A | 8/1938 | Bowen |
| 2,397,823 A | 4/1946 | Walter |
| 2,646,045 A | 7/1953 | Priestly |
| 2,959,172 A | 1/1960 | Held |

(Continued)

FOREIGN PATENT DOCUMENTS

DE    4210724 C1    1/1983

(Continued)

OTHER PUBLICATIONS

Sutura, "A New Choice In Vascular Suturing . . . ", Let Sutura Show You—TCT Booth 846, Fountain Valley, California, www.suturainc.com, 1 page.

(Continued)

*Primary Examiner*—Julian W. Woo

(57) ABSTRACT

Devices, methods, and kits are provided for suturing an end of a first body duct to a hole in the side of a second body duct. The present devices and methods are used to simplify the suturing procedure and thus reduce operating time. In one embodiment, the present device includes a structure for holding the end of the first body duct and positioning the end adjacent to the hole in the side of the second body duct. The structure of the device is typically a shaft having a surface adapted to receive the first body duct. A plurality of needles are arranged on the structure to be advanced along a plurality of paths. Each needle path first passes radially into and forwardly out of the end of the first body duct and into the hole of the second body duct. The path then everts so that the needles and associated sutures will pass outwardly through tissue peripheral to the hole when the end of the first body duct is on the structure adjacent to the hole in the second body duct. The needles preferably travel along such paths when they are advanced forward. In one embodiment, the device uses a J-shaped tube for guiding one of the needles along the desired path. In another embodiment, shape-memory needles having an arcuate profile are used to create the desired path.

35 Claims, 9 Drawing Sheets

U.S. PATENT DOCUMENTS

| | | |
|---|---|---|
| 3,104,666 A | 9/1963 | Hale et al. |
| 3,470,875 A | 10/1969 | Johnson |
| 3,653,388 A | 4/1972 | Tenckoff |
| 3,665,926 A | 5/1972 | Flores |
| 3,776,237 A | 12/1973 | Hill et al. |
| 3,820,544 A | 6/1974 | Semm |
| 3,926,194 A | 12/1975 | Greeenberg et al. |
| 3,939,820 A | 2/1976 | Grayzel |
| 4,018,228 A | 4/1977 | Goosen |
| 4,109,658 A | 8/1978 | Hughes |
| 4,161,951 A | 7/1979 | Scanlan, Jr. |
| 4,168,073 A | 9/1979 | LaRue |
| 4,182,339 A | 1/1980 | Hardy, Jr. |
| 4,216,776 A | 8/1980 | Downie et al. |
| 4,235,177 A | 11/1980 | Arbuckle |
| 4,317,445 A | 3/1982 | Robinson |
| 4,411,654 A | 10/1983 | Boarini et al. |
| 4,412,832 A | 11/1983 | King et al. |
| 4,437,465 A | 3/1984 | Nomoto et al. |
| 4,493,323 A | 1/1985 | Albright et al. |
| 4,553,543 A | 11/1985 | Amarasinghe |
| 4,587,969 A | 5/1986 | Gillis |
| 4,596,559 A | 6/1986 | Fleischhacker |
| 4,629,450 A | 12/1986 | Suzuki et al. |
| 4,651,733 A | 3/1987 | Mobin-Uddin |
| 4,723,549 A | 2/1988 | Wholey et al. |
| 4,738,666 A | 4/1988 | Fuqua |
| 4,744,364 A | 5/1988 | Kensey |
| 4,803,984 A | 2/1989 | Narayanan et al. |
| 4,836,205 A | 6/1989 | Barrett |
| 4,852,568 A | 8/1989 | Kensey |
| 4,890,612 A | 1/1990 | Kensey |
| 4,898,155 A | 2/1990 | Ovil et al. |
| 4,911,164 A | 3/1990 | Roth |
| 4,926,860 A | 5/1990 | Stice et al. |
| 4,929,246 A | 5/1990 | Sinofsky |
| 4,935,027 A | 6/1990 | Yoon |
| 4,957,498 A | 9/1990 | Caspari et al. |
| 4,983,168 A | 1/1991 | Moorehead |
| 4,984,581 A | 1/1991 | Stice |
| 5,002,563 A | 3/1991 | Pyka et al. |
| 5,009,643 A | 4/1991 | Reich et al. |
| 5,021,059 A | 6/1991 | Kensey et al. |
| 5,037,433 A | 8/1991 | Wilk et al. |
| 5,047,039 A | 9/1991 | Avant et al. |
| 5,059,201 A | 10/1991 | Asnis |
| 5,061,274 A | 10/1991 | Kensey |
| 5,078,721 A | 1/1992 | McKeating |
| 5,080,664 A | 1/1992 | Jain |
| 5,100,419 A | 3/1992 | Ehlers |
| 5,100,432 A | 3/1992 | Matsutani |
| 5,109,780 A | 5/1992 | Slouf et al. |
| 5,129,913 A | 7/1992 | Ruppert |
| 5,147,373 A | 9/1992 | Ferzli |
| 5,160,339 A | 11/1992 | Chen et al. |
| 5,171,251 A | 12/1992 | Bregen et al. |
| 5,192,294 A | 3/1993 | Blake, III |
| 5,192,302 A | 3/1993 | Kensey et al. |
| 5,219,358 A | 6/1993 | Bendel et al. |
| 5,222,974 A | 6/1993 | Kensey et al. |
| 5,234,443 A | 8/1993 | Phan et al. |
| 5,242,427 A | 9/1993 | Bilweis |
| 5,250,033 A | 10/1993 | Evans et al. |
| 5,250,053 A | 10/1993 | Snyder |
| 5,254,126 A | 10/1993 | Filipi et al. |
| 5,258,003 A | 11/1993 | Ciaglia et al. |
| 5,279,311 A | 1/1994 | Snyder |
| 5,285,945 A | 2/1994 | Brinkerhoff et al. |
| 5,289,963 A | 3/1994 | McGarry |
| 5,290,284 A | 3/1994 | Adair |
| 5,290,297 A | 3/1994 | Phillips |
| 5,292,309 A | 3/1994 | Van Tassel et al. |
| 5,292,332 A | 3/1994 | Lee |
| 5,293,881 A | 3/1994 | Green et al. |
| 5,295,993 A | 3/1994 | Green |
| 5,300,085 A | 4/1994 | Yock |
| 5,304,184 A | 4/1994 | Hathaway |
| 5,304,185 A | 4/1994 | Taylor |
| 5,306,254 A | 4/1994 | Nash et al. |
| 5,312,024 A | 5/1994 | Grant et al. |
| 5,320,632 A | 6/1994 | Heidmueller |
| 5,336,229 A | 8/1994 | Noda |
| 5,336,230 A | 8/1994 | Adair |
| 5,336,231 A | 8/1994 | Adair |
| 5,342,369 A | 8/1994 | Harryman, II |
| 5,354,312 A | 10/1994 | Brinkerhoff et al. |
| 5,364,408 A | 11/1994 | Gordon |
| 5,368,601 A | 11/1994 | Saver et al. |
| 5,374,275 A | 12/1994 | Bradley et al. |
| 5,376,096 A | 12/1994 | Foster |
| 5,383,896 A | 1/1995 | Gershony et al. |
| 5,387,221 A | 2/1995 | Bisgaard |
| 5,387,227 A | 2/1995 | Grice |
| 5,395,332 A | 3/1995 | Ressemann et al. |
| 5,395,349 A | 3/1995 | Quiachon et al. |
| 5,397,325 A | 3/1995 | Della Badia et al. |
| 5,403,329 A | 4/1995 | Hinchcliffe |
| 5,403,338 A | 4/1995 | Milo |
| 5,411,481 A | 5/1995 | Allen et al. |
| 5,413,571 A | 5/1995 | Katsaros et al. |
| 5,417,699 A | 5/1995 | Klein et al. |
| 5,425,705 A | 6/1995 | Evard et al. |
| 5,431,666 A | 7/1995 | Sauer et al. |
| 5,433,700 A | 7/1995 | Peters |
| 5,452,733 A | 9/1995 | Sterman et al. |
| 5,454,822 A | 10/1995 | Schöb et al. |
| 5,454,834 A | 10/1995 | Boebel et al. |
| 5,458,574 A | 10/1995 | Machold et al. |
| 5,476,469 A | 12/1995 | Hathaway |
| 5,476,470 A | 12/1995 | Fitzgibbons, Jr. |
| 5,478,309 A | 12/1995 | Sweezer et al. |
| 5,478,353 A | 12/1995 | Yoon |
| 5,480,407 A | 1/1996 | Wan et al. |
| 5,486,190 A | 1/1996 | Green |
| 5,489,295 A | 2/1996 | Piplani et al. |
| 5,496,332 A | 3/1996 | Sierra et al. |
| 5,507,744 A | 4/1996 | Tay et al. |
| 5,507,755 A | 4/1996 | Gresl et al. |
| 5,507,757 A | 4/1996 | Sauer et al. |
| 5,507,758 A | 4/1996 | Thomason et al. |
| 5,509,902 A | 4/1996 | Raulerson |
| 5,520,655 A | 5/1996 | Davila et al. |
| 5,520,665 A | 5/1996 | Fleetwood |
| 5,520,702 A | 5/1996 | Sauer et al. |
| 5,527,321 A | 6/1996 | Hinchliffe |
| 5,527,322 A | 6/1996 | Klein et al. |
| D372,310 S | 7/1996 | Harnett |
| 5,531,700 A | 7/1996 | Moore et al. |
| 5,540,701 A | 7/1996 | Sharkey et al. |
| 5,540,704 A | 7/1996 | Gordon et al. |
| 5,545,171 A | 8/1996 | Sharkey et al. |
| 5,545,178 A | 8/1996 | Kensey et al. |
| 5,545,180 A | 8/1996 | Lee et al. |
| 5,549,618 A | 8/1996 | Fleenor et al. |
| 5,554,162 A | 9/1996 | DeLange |
| 5,562,686 A | 10/1996 | Sauer et al. |
| 5,562,688 A | 10/1996 | Riza |
| 5,562,728 A | 10/1996 | Lazarus et al. |
| 5,569,271 A | 10/1996 | Hoel |
| 5,573,540 A | 11/1996 | Yoon |
| 5,591,179 A | 1/1997 | Edelstein |
| 5,591,206 A | 1/1997 | Moufarrege |
| 5,593,421 A | 1/1997 | Bauer |
| 5,603,718 A | 2/1997 | Xu |

| | | |
|---|---|---|
| 5,611,794 A | 3/1997 | Sauer et al. |
| 5,613,974 A | 3/1997 | Andreas et al. |
| 5,613,975 A | 3/1997 | Christy |
| 5,669,917 A | 9/1997 | Sauer et al. |
| 5,700,273 A | 12/1997 | Buelna et al. |
| 5,713,910 A | 2/1998 | Gordon et al. |
| 5,716,369 A | 2/1998 | Riza |
| 5,720,757 A | 2/1998 | Hathaway et al. |
| 5,728,151 A | 3/1998 | Garrison et al. |
| 5,741,276 A | 4/1998 | Poloyko et al. |
| 5,741,280 A | 4/1998 | Fleenor |
| 5,759,188 A | 6/1998 | Yoon |
| 5,766,183 A | 6/1998 | Sauer |
| 5,766,186 A | 6/1998 | Faraz et al. |
| 5,779,719 A | 7/1998 | Klein et al. |
| 5,792,151 A | 8/1998 | Heck et al. |
| 5,799,661 A | 9/1998 | Boyd et al. |
| 5,810,850 A | 9/1998 | Hathaway et al. |
| 5,817,113 A | 10/1998 | Gifford, III |
| 5,820,631 A | 10/1998 | Nobles |
| 5,824,010 A | 10/1998 | McDonald |
| 5,836,955 A | 11/1998 | Buelna et al. |
| 5,836,956 A | 11/1998 | Buelna et al. |
| 5,846,253 A | 12/1998 | Buelna et al. |
| 5,860,990 A | 1/1999 | Nobles et al. |
| 5,902,311 A | 5/1999 | Andreas et al. |
| 5,904,697 A | 5/1999 | Doi et al. |
| 5,951,590 A | 9/1999 | Goldfarb |
| 5,954,732 A | 9/1999 | Hart et al. |
| 6,036,699 A | 3/2000 | Andreas et al. |
| 6,048,351 A | 4/2000 | Gordon et al. |
| 6,117,144 A | 9/2000 | Nobles et al. |

FOREIGN PATENT DOCUMENTS

| | | | |
|---|---|---|---|
| DE | 9217932 | | 7/1993 |
| EP | 01407557 A | | 5/1985 |
| EP | 207545 A1 | | 1/1987 |
| EP | 0474 887 A1 | | 3/1992 |
| EP | 0478 358 A1 | | 4/1992 |
| EP | 0589 409 A1 | | 9/1992 |
| EP | 0624 343 A2 | | 4/1993 |
| EP | 0542 126 A3 | | 5/1993 |
| EP | 0568 098 A2 | | 11/1993 |
| EP | 669103 A1 | | 8/1995 |
| EP | 568098 B1 | | 10/1997 |
| EP | 669102 B1 | | 10/1998 |
| EP | 669101 B1 | | 9/1999 |
| FR | 1059544 | | 7/1952 |
| JP | 405042161 | | 2/1993 |
| RU | 820810 | | 6/1997 |
| SU | 993922 | | 2/1983 |
| SU | 1093 329 A | | 5/1984 |
| SU | 1174 036 A | | 8/1985 |
| SU | 1544383 | | 2/1990 |
| SU | 1648400 | | 5/1991 |
| WO | WO 94/27503 | | 6/1993 |
| WO | WO 94/28801 | | 6/1993 |
| WO | WO 95/05121 | | 8/1993 |
| WO | 9405213 | | 3/1994 |
| WO | WO 95/35065 | | 12/1995 |
| WO | WO 97/03613 | | 2/1997 |
| WO | WO 97/10764 | | 3/1997 |
| WO | WO 97/13461 | | 4/1997 |
| WO | WO 97/17901 | | 5/1997 |
| WO | WO 97/20505 | | 6/1997 |
| WO | WO 00/12013 | | 3/2000 |

OTHER PUBLICATIONS

Elgiloy Brochure, Elgin National Watch Co., Elgin IL *Jun. 23, 1959).

Product Brochure "The Proven Solution to Endoscopic Suturing", Laurus Medical Corp., Irvine CA (Oct. 1994).

Datascope Corporation, Montvale, NJ, American Heart Assoc. Meeting \, Anaheim 1 page (1991).

Kensey Nash Corporation, Exton PA, "The Hemostatic Puncture Closure Device", 2 pages.

"Innovation Through Progress", REMA-Medizintechnik, GMBH, Jan. 1992.

AD: The laurus In-Line Endoscopic Suturing Device (The Laurus ND—2600 Needle Driver), Laurus Medical Corp., Rev. Oct. 1994.

Cardiac Catheterization and Andgiography, $3^{rd}$ Ed., Lea & Fabiiger, Philadelphia 1986.

Cardio-Thoracic Systems Prospectus dated Mar. 20, 1996.

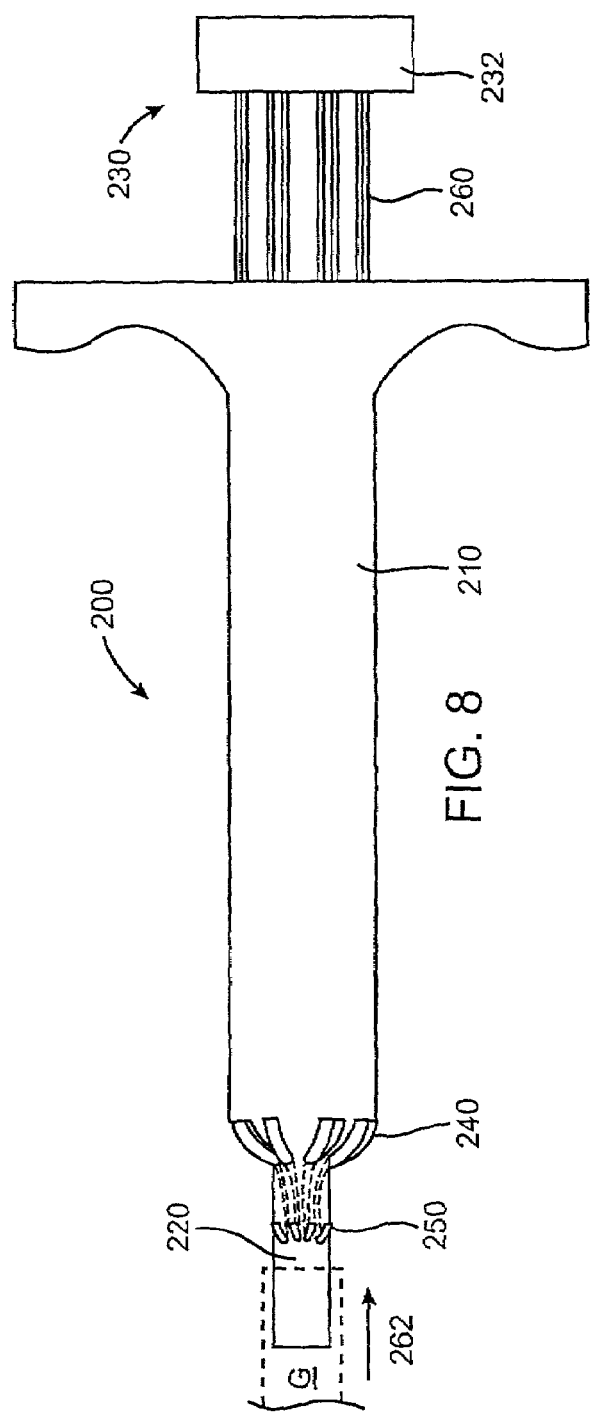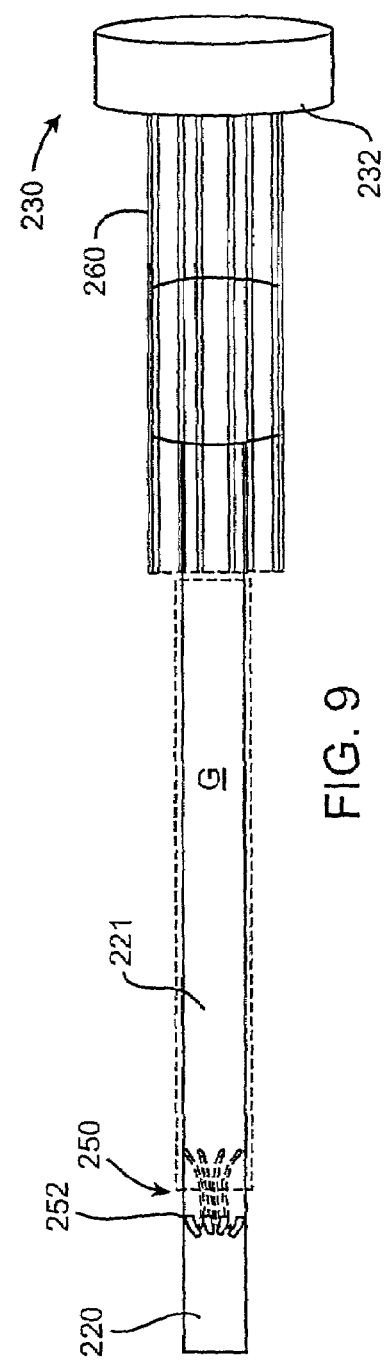

DEVICE AND METHOD FOR PERFORMING END-TO-SIDE ANASTOMOSIS

CROSS-REFERENCES TO RELATED APPLICATIONS

This application is a in continuation divisional of Application Ser. No. 09/395,901, filed on Sep. 14, 1999 now U.S. Pat. No. 6,358,258.

BACKGROUND OF THE INVENTION

The present invention relates generally to devices and methods for suturing body tissue. More particularly, the present invention is useful for performing end-to-side attachments of body ducts, such as in suturing coronary blood vessel grafts.

In many medical procedures today, it is desirable to connect a body duct, such as a hollow organ or blood vessel, to a targeted piece of tissue. In coronary surgery, this type of attachment is commonly referred to as an anastomosis. In certain heart operations where coronary artery bypass graft surgery ("CABG") is performed as shown in FIG. 1A, a graft blood vessel G may be affixed to a port or aperture in an arterial wall of an artery to supply blood downstream of a blockage in another blood vessel V. The proximal end of the blood vessel graft is typically connected to a pressurized arterial blood supply, such as the aorta A, while the distal end is coupled to the vessel lumen downstream of the blockage. The amount of time spent performing these anastomosis procedures to connect blood vessel grafts between blocked arteries and pressurized blood supplies is critical to patient mortality and morbidity. In conventional CABG surgery, three critical determinates that affect the outcome of a bypass surgery are (1) time the patient spends on cardiopulmonary bypass, (2) time the patient spends with a clamped aorta, and (3) the quality of the anastomosis. It is generally understood that the risk of patient morbidity rises significantly after a threshold time of one hour on cardiopulmonary bypass. Continual circulation of blood through the mechanical apparatus of the bypass machine can cause various degradations to the blood. Perhaps the most prevalent complication arising from prolonged cardiac bypass is the high risk of distal thrombosis, which can embolize into the neurovasculature and potentially cause a stroke.

A critical factor in reducing the amount of time a patient spends on bypass is directly related to the time spent anastomosing the blood vessel grafts used during surgery. The average time for suturing one anastomosis is approximately seven to ten minutes. It is believed that an average CABG procedure involves approximately five anastomoses. Therefore, the average time for graft suturing ranges from thirty-five to fifty minutes, which is a significant portion of the sixty-minute threshold for patient morbidity. Patients treated with conventional coronary surgery and placed on cardiopulmonary bypass would benefit from reducing the amount of time spent performing each anastomosis.

In "off pump" procedures where patients are not placed on cardiopulmonary bypass and the heart remains beating, the difficulty of suturing an anastomosis graft on a moving surface of the heart may degrade the quality of such grafts completed on patients. "Off pump" procedures do not use cardiopulmonary bypass pumps or devices and thus reduces the blood damage associated with bypass devices. "Off pump" procedures, however, requires a higher degree of expertise to perform coronary artery bypass grafts on a beating or moving object. An anastomosis differs from straight line suturing in that each suture has a different orientation that is based on its position around the cross-sectional circumference of the blood vessel graft. It can be appreciated that some of the sutures are easily made from on top of the conduit or blood vessel graft, while others are more difficult to complete as they are beneath the conduit. It can be further appreciated that performing such complex suturing procedures on a moving platform, such as the beating heart, further increases the difficulty associated with such suturing procedures. Improperly connecting blood vessel grafts to the patient may present substantial post-operative complications and/or increase operating room time spent correcting the improperly connected graft.

Accordingly, it would be desirable to provide improved devices and methods that simplify anastomosis graft procedures performed on patients, particularly where multiple graft procedures are to be performed. Simplifying the anastomosis procedure would typically reduce the time spent on each graft and thus minimize the time a patient spends on cardiopulmonary bypass. Additionally, it would desirable to provide a device that improves the consistency of the suture pattern created during each anastomosis graft.

SUMMARY OF THE INVENTION

The present invention comprises systems, methods, and kits for facilitating the suturing of one body duct to another body duct or tissue surface. The present invention simplifies suture delivery, reducing the amount of time required for performing an anastomosis and facilitating the delivery of suture needles through blood vessels. The present invention may be used in a variety of environments and is applicable to both stopped heart and beating heart procedures. The prevent invention may be used in a minimally invasively environment using percutaneous ports such those developed by Heartport, Inc. of Redwood City, Calif. or retractor systems developed by Cardio Thoracic Systems of Cupertino, Calif. Of course, the present invention may also be used in an open surgery environment.

The present invention preferably allows the delivery of a plurality of needles through both body ducts in a single continuous motion by the user. Advantageously, this simplified needle/suture delivery reduces the amount of time spent on performing body duct connections such as an anastomosis. In situations where the invention is used with a beating heart, the invention allows for rapid actuation once the device is properly positioned, reducing the likelihood that movement of the beating heart may misposition the device during actuation. The present invention further allows for the simultaneous delivery of a plurality of needles through the body ducts in an evenly-spaced manner which thus improves the quality of the anastomosis by having a consistent suture pattern and a calculated tissue capture. The present invention is also particularly useful when targeting a pressurized blood vessel when it is desirable to maintain hemostasis at the targeted suture site.

In one aspect of the present invention, a device is provided for suturing one end of a first body duct to a hole in the side of a second body duct. When performed during coronary surgery, such connections of the body ducts are known as end-to-side anastomoses. The device according to the present invention includes a structure for holding the end of the first body duct and positioning the end adjacent to the hole in the side of the second body duct. The structure of the device is typically a shaft having a surface adapted to receive the first body duct. The first body duct used during anastomosis is typically some type of tubular graft such as a saphenous vein while the second body duct is the targeted blood vessel. Further examples of first and second body ducts are provided in the detailed description below.

A plurality of needles are arranged on the structure to be advanced along a plurality of paths. FIG. 1B depicts preferred paths according to the present invention. Each needle path first passes radially into and forwardly out of the end of the first body duct and into the hole of the second body duct. The path then everts so that the needles and associated sutures will pass outwardly through tissue peripheral to the hole when the end of the first body duct is on the structure adjacent to the hole in the second body duct. The needles preferably travel along such paths when they are advanced forward. The structure of the device typically includes a plunger which may be translated to advance the needles forward through the first body duct. The plunger may include suture storage area for sutures attached to the needles.

The needle paths of the present invention may be defined in a variety of manners. In one embodiment of the present invention, a plurality of guide channels are provided to define the path of the needles. The channels may be integrally formed in the device structure or they may be individual guide tubes. The guide channels typically have a first portion and a second portion where the first and second portions are separated by a gap which receives the end of the first body duct. The first portion of the guide channel is adapted to be positioned outside the first body duct and has a distal opening positioned to open towards an outer surface of the first body duct when the first body duct is mounted on the structure, between the gap. The second portion of the guide channel is adapted to be positioned in the lumen of the first body duct when the first body duct is mounted on the structure within the gap.

The needles are advanced from the first portion of the guide channel to pass through the body duct wall and into the second portion of the guide channel. The needles are preferably of sufficient length to extend through the guide channels and through the tissue layer of the second body duct. The second guide channel preferably has a J-shaped section to guide the needle along the desired path. The needles passing through the J-shaped section will assume an everted configuration directing the needles toward peripheral tissue around the hole in the second body duct. The guide channel or tube may also have a longitudinal slot extending along a portion of the channel or tube to facilitate removal of the suture once the needle has been removed from the guide channel. To facilitate delivery through the curved portions of the guide channel, the needles used in the guide channels are typically made of materials such as a shape-memory alloy or a superelastic material.

In another embodiment of the suturing device, the present invention uses a plurality of needles having an arcuate profile-when unconstrained to define the needle path. The needles are constrained by a tubular constraint on the structure and the needles are movable between a first position and a second position. In the first position, the tubular constraint maintains the needles in a substantially straight configuration. In the second position, the needles are advanced forward and extend beyond the tubular constraint, assuming the arcuate profile. The tubular constraint typically comprises an outer tube and an inner tube. The outer tube has a passage with the inner tube slidably mounted within that passage. As seen in the figures, the tubes are typically coaxially aligned and have a slideable relationship relative to each other. In this embodiment, the needles are fixedly secured to the distal end of the inner tube so that the needles are adapted to penetrate one end of the first body duct when the body duct is mounted within the inner tube. When the needles assumes the arcuate profile, the sharpened distal tips of the needle preferably point in a proximal direction towards tissue peripheral to the hole in the second body duct.

In another aspect of the present invention, a method is provided for suturing one end of a first body duct to a hole in the side of a second body duct. Although not limited in this manner, such suturing is particularly suited for performing an anastomosis graft during coronary surgery. The method involves positioning one end of the first body duct adjacent to the hole in the second body duct. A plurality of needles are advanced, carrying a plurality of sutures along a plurality of paths. Needles following each path first passes radially into and forwardly out of the end of the first body duct and into the hole of the second body duct and then everts to pass outwardly through tissue peripheral to the hole when the end of the first body duct is on the structure adjacent to the hole in the second body duct. A portion of at least one of the sutures is secured outside of the first body duct to a portion of the suture outside of the peripheral tissue surrounding the hole in the second body duct. Typically, the first body duct is mounted against a shaft structure containing the plurality of needles. This may involve placing the body duct over a portion of the shaft structure or placing the body duct within a lumen of the shaft structure.

The method typical involves advancing a plunger or similar device to drive the needles along the desired path. In one embodiment, advancing the needles involves passing the needles through guide channels which define the paths. The guide channels each have a first portion and a second portion, where the first and second portions are separated by a gap which receives the end of the first body duct. Advancing the needle typically comprises passing the needle through the first portion of the guide channel, through the wall of said first body duct, and into the second portion of the guide channel. As the needles are advanced, they will also be everted. The second portion of the guide channel has a curved portion which will bend the needle to have a partially everted configuration. Securing the sutures involves removing the sutures from the guide channels by lifting the sutures out of the channels through a longitudinal slot running along a length of at least one of the guide channels.

In another embodiment, the prevent invention provides another method for everting the needles as they are advanced. The needles used in this method have arcuate profiles when unconstrained. The everting comprises passing the needles forwardly from a tubular constraint so that the needles assume an everted configuration as they are passed forwardly. Typically, the method involves providing a suturing device having two coaxially-mounted tubes where at least one of the needles is made of a shape-memory alloy and is mounted on the inner tube. The needles are extended beyond the outer tube by relative motion between the needle and the outer tube where the needle is extended to the arcuate configuration, preferably where a sharpened tip of the needle points substantially in a proximal direction. It may be necessary to lift the shaft structure in a proximal direction to pull the needles through the peripheral tissue surrounding the hole in the second body duct.

Kits according to the present invention will comprise a graft suturing device which delivers a plurality of needles. The kits will further include instructions for use setting forth a method as described above. Optionally, the kits will further include packaging suitable for containing the graft device and the instructions for use. Exemplary containers include pouches, trays, boxes, tubes, and the like. The instructions for use may be provided on a separate sheet of paper or other medium. Optionally, the instructions may be printed in whole or in part on the packaging. Usually, at least the graft suturing device will be provided in a sterilized condition. Other kit components, such as the graft to be sutured, may also be included.

A further understanding of the nature and advantages of the invention will become apparent by reference to the remaining portions of the specification and drawings.

BRIEF DESCRIPTION OF THE DRAWINGS

FIG. 8 shows another embodiment of the suturing device according to the present invention;

FIG. 9 illustrates internal mechanisms of the suturing device shown in FIG. 8;

DESCRIPTION OF THE SPECIFIC EMBODIMENTS

The present invention is directed towards devices and methods for facilitating the suturing of one body duct to another body duct. In particular, the present invention will facilitate the end-to-side or end-to-end anastomosis of a vascular graft such as a saphenous vein to a target artery such as the aorta or similar blood vessel. Usually, a vascular graft will have a width in the range from 2 mm to 8 mm, while the target will have a width from 2 mm to 5 mm. The aorta will have a width from 20 mm to 40 mm. As described below, devices of the present invention can preferably deploy a plurality of needles in an evenly spaced or otherwise predetermined configuration to perform the anastomosis. In exemplary embodiments, a device of the present invention can position the suture for performing the end-to-side anastomosis through one hand stroke or step by the user. Deployment of a plurality of needles in a predetermined pattern increases the likelihood that the anastomosis will have sufficient patency to channel blood as desired and have reduced incidence of fluid leakage. More importantly, however, the present device will reduce the amount of time a patient spends on a cardiopulmonary bypass, which has a direct relationship to a patient's operative and peri-operative morbidity. The reduced number of steps required for a user to perform the anastomosis also lends the present device for use in beating heart or off-pump procedures.

The term "body duct" as used herein is generally in reference to a blood vessel such as those listed on Table 1. It should be understood, however, that the term is intended to cover a variety of body lumens and may refer to non-vascular body lumens such as the bile duct, the urethra, the urinary bladder, or other body lumens which require assistance to be rejoined. Graft vessels and ducts can be natural or synthetic, preferably being natural vessels obtained from the patient being treated. Typically target blood vessels and graft vessels are provided in the table below.

TABLE 1

| TARGET VESSELS | GRAFT VESSELS |
|---|---|
| Coronary arteries | Internal mammary artery |
| Coronary artenes | Saphenous veins |
| Aorta | Saphenous veins |
| Femoral artery | Saphenous veins |
| Popliteal artery | Saphenous veins |

Figure 1A:
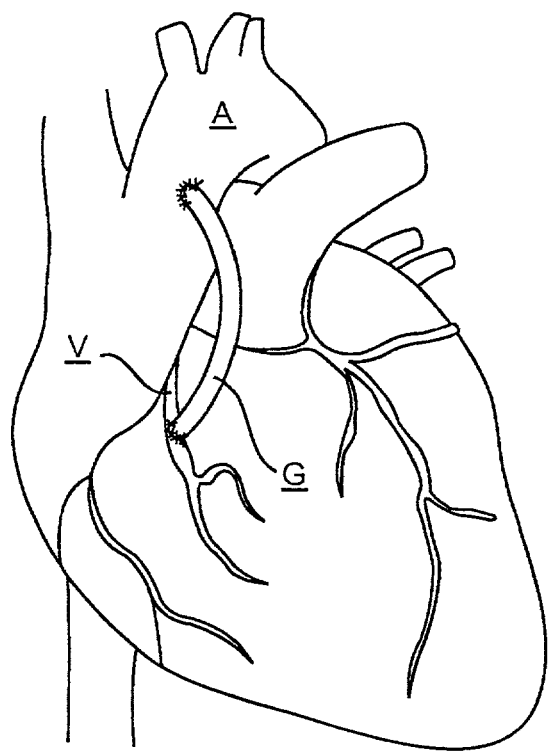
FIG. 1A shows one blood vessel grafted onto various blood vessels of the heart.
Figure 1B:
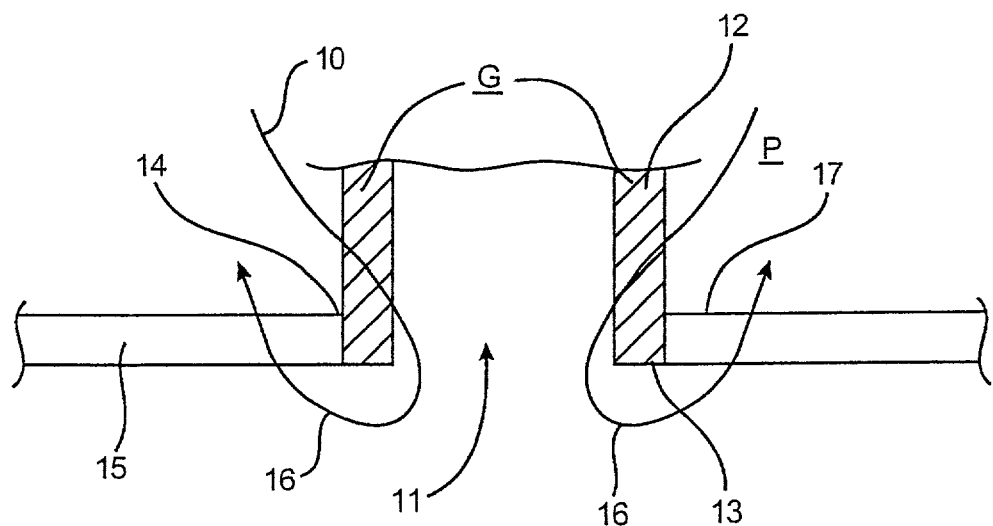
FIG. 1B is a cross-sectional view showing the suture path used to connect two body ducts together.

The present invention is particularly useful in attaching a tubular graft to the side of another tissue structure as shown in FIG. 1B. The present invention relies on delivering a plurality of needles through the body ducts along a substantially everted J-shaped or hooked suture path P as shown in FIG. 1B. Each path P first passes the needle radially into and forwardly out of the end of the first body duct and into the hole of the second body duct and then everts so as to pass outwardly through tissue peripheral to the hole when the end of the first body duct is on the structure adjacent-to the hole in the second body duct. This advantageously allows the graft body duct to be connected to the targeted body duct in a minimal amount of time using sutures, while possibly increasing the quality and accuracy of the luminal graft.

In particular, the present invention provides devices, kits, and methods for their use which deliver the sutures along defined paths in relation to blood vessels or other body ducts. The paths will each include an initial portion 10 where the suture is introduced radially inwardly so that it passes into the distal lumen of a first body duct, usually within 0.25 mm to 1.5 mm of the distal terminus 13. The distal terminus of the first body duct will be positioned adjacent to-the hole 14 in the second body duct 15, and the sutures will pass inwardly through the hole and will then evert along radially outward portions 16. Such everting paths allow the suture to pass through a peripheral edge 17 of the wall of the second body duct 15 surrounding the hole 14, typically within 0.25 mm to 1.5 mm of the hole. Usually from 4 to 20 sutures will be positioned, preferably from 8 to 12. Usually, but not necessarily, sutures will be positioned simultaneously. After positioning, sutures can be individually tied off to complete the anastomotic attachment.

Figure 2:
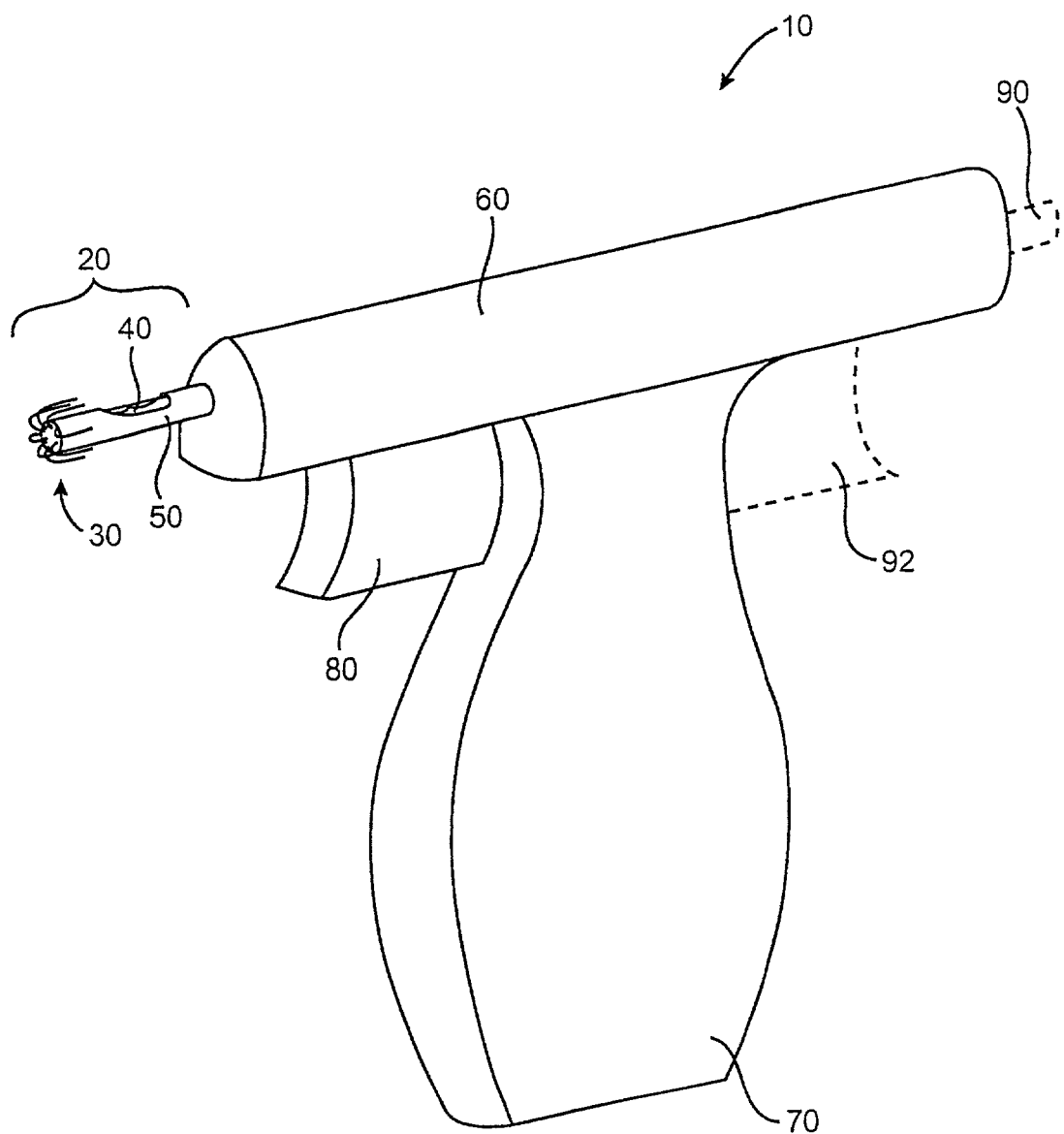
FIG. 2 depicts a preferred embodiment of the present invention having a plurality of needles extended in a substantially curved configuration.

Referring now to FIGS. 2–7, one embodiment of a suturing device 10 for use in coronary graft anastomosis will be described in further detail. Although the remainder of the application discusses the invention in coronary surgery environment, it should be understood, of course, that the device can be adapted for use in a variety of other surgical settings such as laparoscopic environments and the like. As shown in FIG. 2, the suturing device 10 has a shaft structure 20 for deploying a plurality of needles 30 to perform the anastomosis. The needles 30 are typically mounted in a radial configuration about the shaft structure 20. The radial configuration is used to improve tissue capture and spacing during suture placement and needle deployment. In the present embodiment, the shaft structure 20 comprises an inner tube 40 coaxially mounted within an outer tube 50. The outer tube 50 acts as a tubular constraint that contains the needles 30 that are typically mounted on the distal end of the inner tube 50. Although FIG. 2 shows tubes 40 and 50 as rigid structures, it should be understood that the tubes 40 and 50 may be replaced by structures having different configurations and stiffnesses such as coaxially mounted tubular catheters. The inner tube 40 and outer tube 50 are preferably coaxially aligned and are slideable relative to one another. This slideable relationship may involve moving the outer tube 50 relative to the inner tube 40 or vice versa. The tubes 40 and 50 may also be substantially longer than those shown in FIG. 2.

The shaft structure 20 is typically mounted on the distal end of elongate housing 60. As shown in FIG. 2, the elongate housing 60 is preferably connected to an ergonomic handle 70 which allows for both left-handed and right-handed use. A trigger 80 may be depressed to reciprocate the tubes 40 and 50 relative to one another. Typically, the inner tube 40 is reciprocated by actuation of the trigger 80. The outer tube 50 may be coupled to a plunger that reciprocates the tube between a first and second position. As shown by phantom lines in FIG. 2, the suturing device 10 may also include a second shaft structure 90 and a trigger 92 for performing anastomosis on the other end of the graft body duct G. It should be understood that the shaft structure 90 may use needle delivery mechanisms different than that disclosed for the shaft structure 20. For example, a suturing mechanism such as that described in commonly assigned, co-pending U.S. patent application Ser. No. 08/883,246 (Attorney Docket No. 15508-000150) filed on Jun. 26, 1997, the full disclosure of which is incorporated herein by reference, may also be used. Having dual suturing mechanisms on the same anastomosis device may reduce the amount of time required to perform the procedures on the patient. The housing 60, the ergonomic grip 70, and the trigger 80 may be made of a variety of materials such as stainless steel or a medical grade polymer to reduce the weight of the device. A variety of other actuating mechanisms beside the trigger 80, such as a pistol grip having a pivot trigger or a motorized drive mechanism, may also be used.

Figure 3:
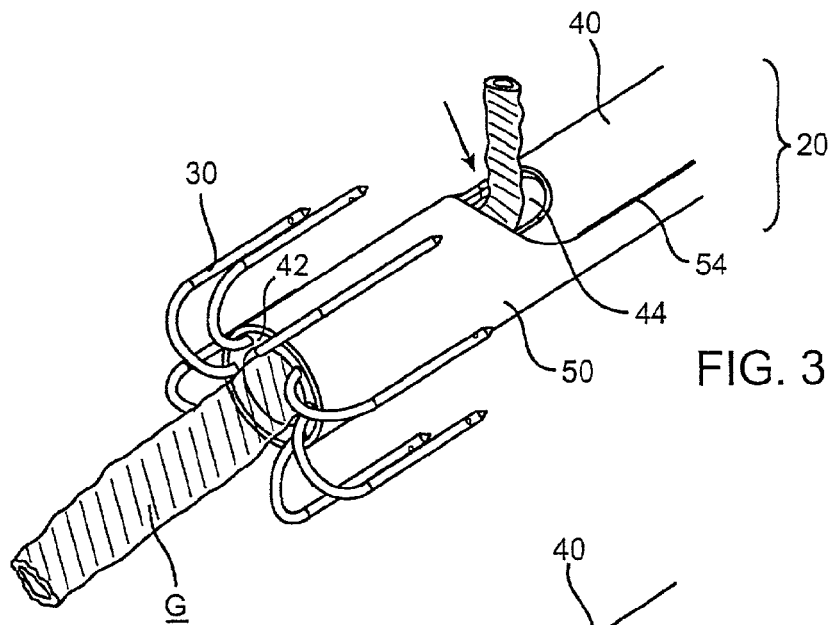
FIGS. 3–7 show the loading of a body graft and needle delivery using a device as illustrated in FIG. 2.

Referring now to FIG. 3, a suturing procedure using the shaft structure 20 will now be described. FIG. 3 shows a perspective view of the shaft structure 20 having a graft body duct G loaded into the structure. In this embodiment, the inner tube 40 has a lumen with a cylindrical surface that receives the graft body duct G. The curved needles 30 are typically attached to a distal end 42 of the inner tube 40. The needles have an arcuate profile as shown in FIG. 3 when the needles are unconstrained. In FIG. 3, the outer tube 50 is retracted or otherwise positioned to unsheathe the needles 30 so that they may assume their substantially curved configuration or arcuate profile. The inner tube 40 has an opening 44 and the outer tube 50 has an opening 54 which allow a proximal end of the body graft G to protrude from the shaft structure 20. These openings 44 and 54 facilitate the loading of the body graft G into the shaft structure 20. The graft G may be backloaded through the distal end of the inner tube 40 or loaded in a forward direction through the opening 44 in the side of the inner tube 40. As seen in the figure, the body graft G is typically positioned adjacent to the tubular structure having the needles 30.

Figure 4:
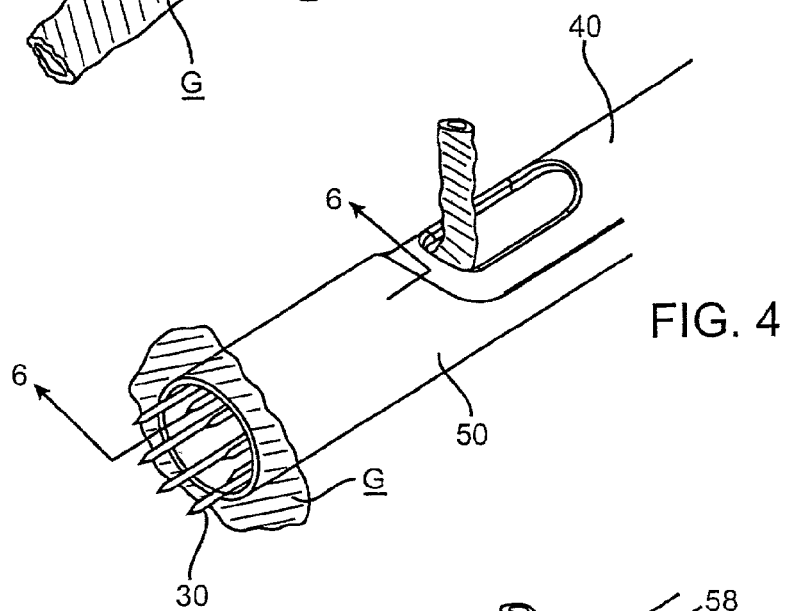

Referring now to FIG. 4, with the body graft G properly positioned, the outer tube 50 is advanced to a second position (or the inner tube 40 retracted) which sheathes the needles 30 and places them in a substantially straight configuration. It should be understood, of course, that such relative motion between the tubes may also be accomplished by retracting the inner tube 40. With the needles 30 substantially or completely sheathed, the graft body duct G may be mounted onto the needles by various methods such as everting the graft body duct G as shown in FIG. 4. The needles 30 are typically advanced forward through the graft body duct G. This loading of the graft body duct G and penetration by needles 30 typically occurs in a bench environment outside the patient prior to the anastomosis procedure. A variety of needle guides or graft holders may be used to facilitate the initial penetration of the graft body duct G by the needles 30.

Figure 5:
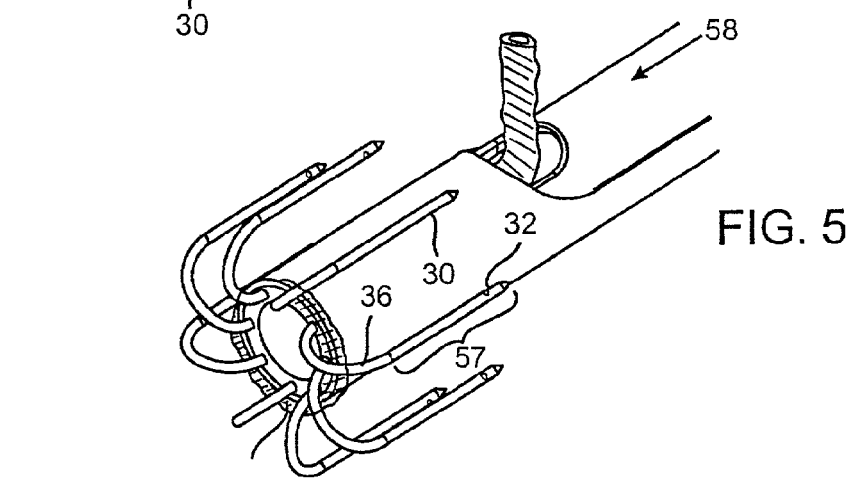

As shown in FIG. 5, the inner tube 40 may be advanced as indicated by arrow 58 (or the outer tube 50 may be retracted) to drive the needles through the graft body duct G and to expose the needles in their substantially curved configuration. As can be seen in FIG. 5, the needles have a through hole 32 on which a suture may be attached. Typically, this through hole 32 is located near the sharpened tip of the needle. In a preferred embodiment, the needles are made of shaped memory material such as a nickel titanium alloy or similar material. In this preferred embodiment, the needle 30 has a diameter of 0.014 inches having a U-shaped bend diameter of approximately 3.1 mm. The length of the needle minus the bend 56 as indicated by bracket 57 is approximately 5 mm. Although this is the preferred length for penetrating the tissue wall of an aorta A, it should be understood that the length of the needle may be varied as desired to penetrate a targeted tissue wall. The inner tube 40 and outer tube 50 may be made of a variety of materials such as stainless steal or various medical grade polymers. The inner tube 40 has an inner diameter of approximately 3.18 mm and the outer diameter of 4.11 mm. The outer tube 50 typically has an inner diameter of 4.14 mm and an outer diameter of 4.65 mm. These tubes 40 and 50 may be sized as desired based on their intended usage.

Figure 6:
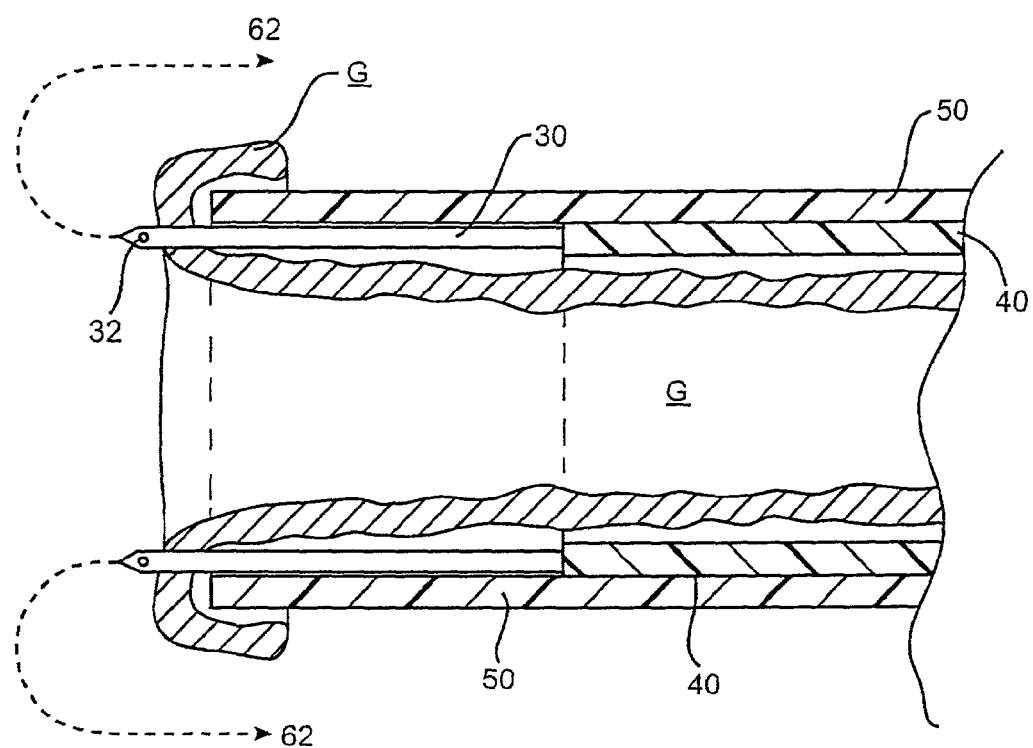

FIG. 6 shows a cross-section of the shaft structure 20, as indicated by lines 6—6 in FIG. 4, with the graft body duct G loaded therein. The needles 30 mounted on the inner tube 40 penetrate through the wall of the graft body duct G. The end of the graft G is everted over the end of the outer tube 50. This helps the needles 30 penetrate the graft G. When the outer tube 50 moves relative to the inner tube 40, the needles will begin to curve and travel along the path indicated by phantom lines 62.

Figure 7A:
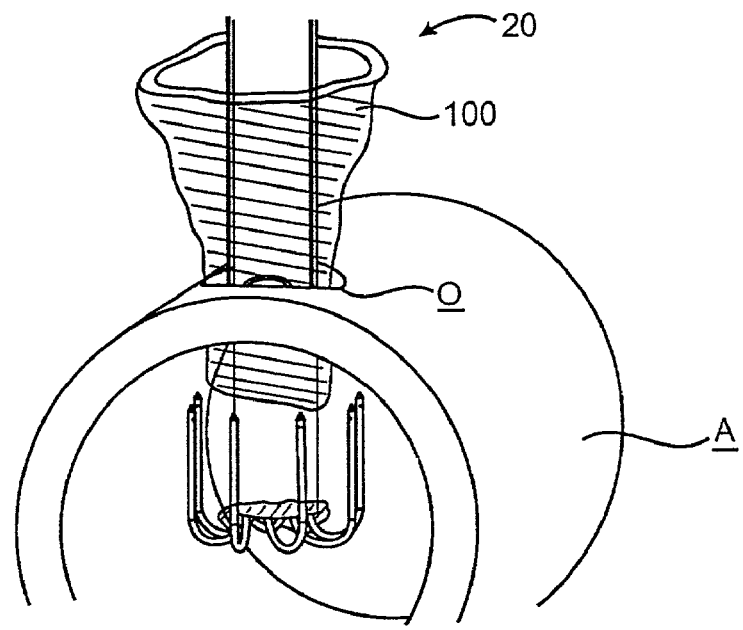
Figure 7B:
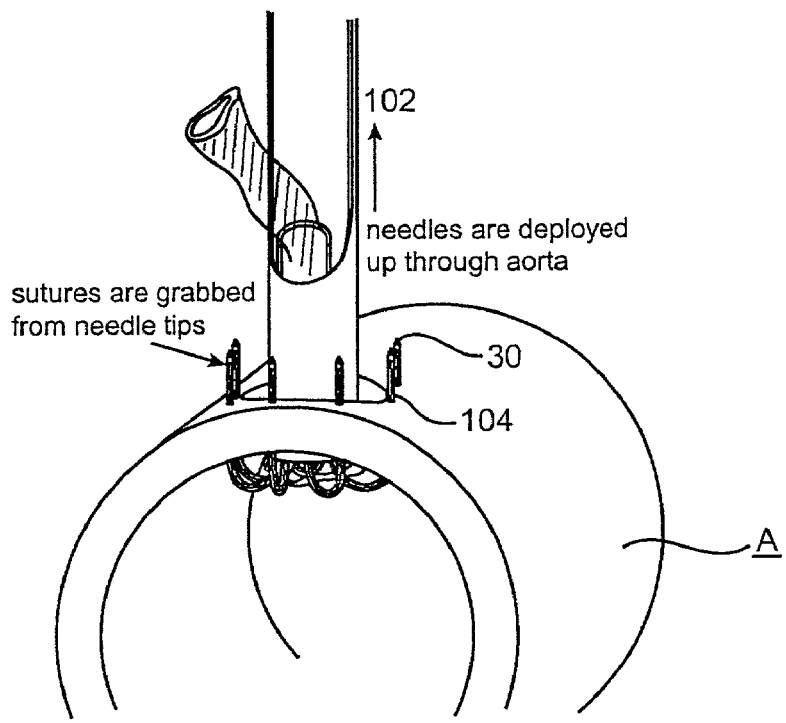

As shown in FIGS. 7A and 7B, when the sutured device 10 is used to graft a graft body duct G to the aorta A, a penetration of approximately 4.5 mm in diameter for the present embodiment is punched into the aorta wall. A breakaway catheter or similar sheathing device 100 is typically used to facilitate entry of the shaft structure 20 in a minimally traumatic manner into the aorta A. Preferably the shaft structure 20 is inserted into the aorta A with the needles in a sheathed, substantially straight configuration. Once inside the lumen of the aorta, the needles are fully extended by retracting the outer tube 50, exposing the needles in their substantially curved configuration as shown FIG. 7A. As shown in FIG. 7B, the breakaway catheter 100 is removed and the entire shaft structure 20 is pulled proximally as indicated by arrow 102 such that the needles 30 penetrate the aorta wall exposing the sharpened tips of the needles. Alternatively, the needles may be deployed from their substantially straight configuration near the wall of the aorta so as to curve upward and through the aorta wall without substantial movement of the shaft structure 20 in the proximal direction 102. Once the needles have penetrated the aorta wall, the sutures 104 held with an opening 32 may be grabbed and removed from the needle tips for knotting to complete the anastomosis. The shaft structure 20, of course, is removed by lowering the shaft structure 20 into the aorta lumen, returning the needles to their substantially straight configuration within the inner tube 50 and withdrawing the shaft structure 20 from the aorta prior to completion of the anastomosis. It should be understood that during the delivery of the needles 30 through the aorta wall, a variety of other instruments, such as a vacuum plate or other material, may be used to support the peripheral tissue around the hole or opening O to facilitate penetration by the needles 30. Upon penetration of the aorta tissue, the needle should create a suture path similar to that shown in FIG. 1B. Such a J-shaped suture path is created by pushing a needle along a path through the end of the first body duct inwardly through the hole in the aorta, and then retracting the needle so they penetrate outwardly through peripheral tissue surrounding the hole in the aorta. The sutures may then be secured to attach the graft body duct.

Referring now to FIGS. 8 through 14, another embodiment of a suturing device according to the present invention will be described in further detail. As shown in FIG. 8, a suturing device 200 of the present invention has a housing 210, a shaft structure 220, and a plunger assembly 230 having a thumb cap 232. In the present embodiment, the suture device 200 has a guide channel having a first portion 240 and a second portion 250. These channels 240 and 250 are used to guide needles of the device 200 along a path similar to that shown in FIG. 1B. The guide channels 240 and 250 may be integrally formed in the shaft structure 220 or they may be individual tubular structures. As discussed in regards to FIG. 11, the second portion 250 of the guide channel preferably has a substantially curved configuration to guide the needles along the desired path. The needles contained in the first portion 240 of the guide channel in housing 210 are made of materials such as nickel titanium (NiTi) alloy so as to provide sufficient flexibility to pass through the curved portions of the guide channels. Of course, the needles may also be made of a variety of other superflexible or shape memory materials. The elongate members or drive tubes 260 coupled to the plunger 230 can be advanced to drive the needles through the channels in the housing 210 and through the portions 240 and 250.

Figure 10:
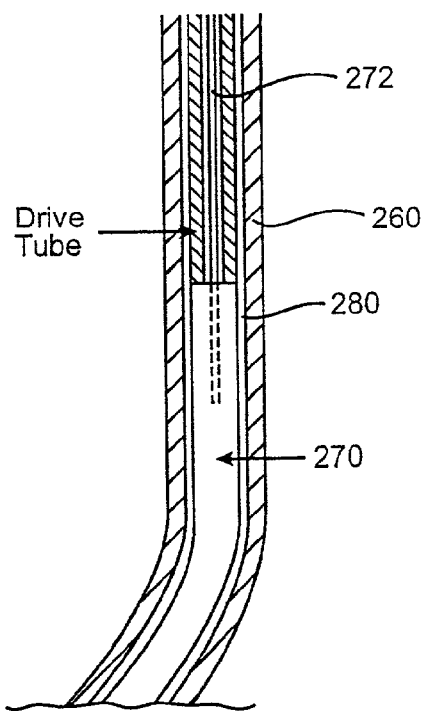
FIG. 10 is a cross-sectional view of a first tube containing the needle and drive tube.

The graft G shown in phantom in FIG. 8, is typically loaded onto the device 200 by sliding the graft along the shaft structure 220 as indicated by arrow 262. FIG. 9 shows the suturing device 200 with the housing 210 removed to better illustrate the shaft structure 220, plunger 230, and position of the graft G when loaded. As shown in phantom in FIG. 9, the graft body duct G is loaded onto the shaft structure 220 so that the graft G preferably does not cover openings 252 of the channels 250. The shaft structure 220 has a surface 221 adapted to receive the graft body duct G. Although the device 200 of FIG. 8 shows the present device with a syringe-type configuration, it should be understood that a variety of other driving mechanisms, such as a ratcheting pistol grip or a motorized needle driver, may be used to deploy the needles of the present invention. As seen in FIG. 10, the elongate members or drive tubes 260 contact the flexible needles 270 to advance the needles through a guide tube 280 or channel within the housing 210. Each needle 270 preferably carries a suture 272 that is secured near the proximal end of the needle. In preferred embodiments, the suture 272 extends within a lumen of the elongate member 260. The plunger 230 and/or the thumb cap 232 typically acts as suture storage areas for the needles 270 of the present device. It should be understood, of course, that in alternative embodiments, the suture 272 may also be connected to the sharpened distal tip of the needle 270.

Figure 11:
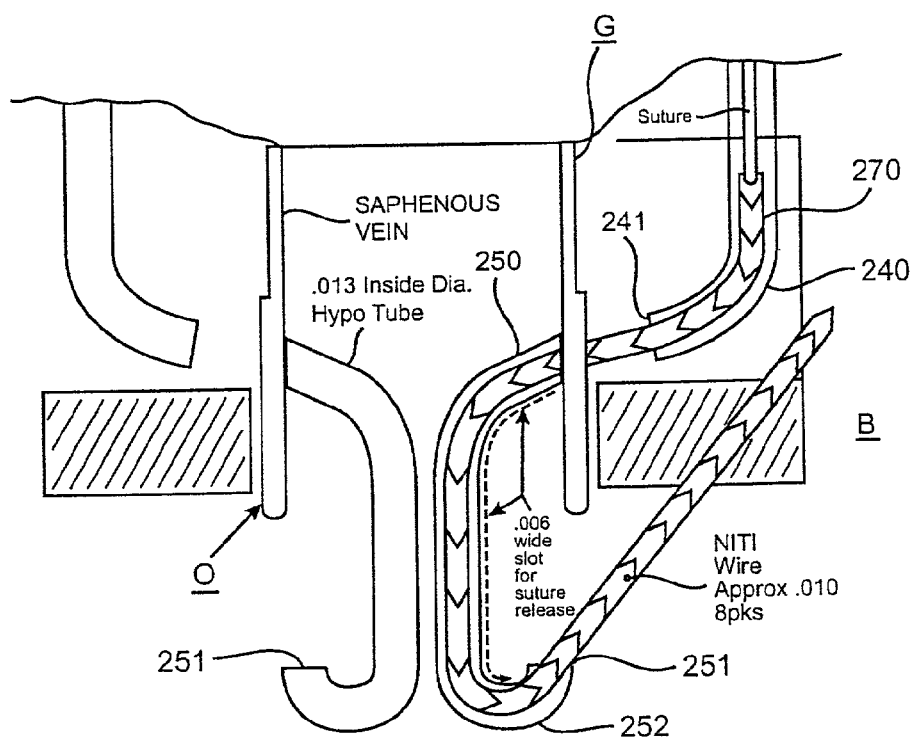
FIGS. 11–12 illustrate needle delivery through two body ducts using the device of FIG. 8.

Referring now to FIG. 11, a cross-sectional view of the distal tip of device 200 will now be described. As seen in the figure, needle 270 is advanced through the first portion 240 of the guide channels. The first portion 240 is located on an outer side of the graft body duct G and has an opening 241 positioned to open towards the graft body duct G. The needle 270 passes through the wall of graft G and into the second portion 250 of the guide channel located on the inner side of the graft. The needle 270 is of sufficient flexibility to pass through the preferably curved configuration of the second portion 250 and out the opening 251. In preferred embodiments, the second portion 250 has a J-shaped section to evert needles passing through the guide channel. The needle 270 is everted at bend 252 which directs the needle outward towards tissue peripheral to an opening O made in a targeted body duct such as the aorta. The sharpened distal end is pointed proximally towards the tissue surrounding the opening O in the second body duct B. Preferably, the needle 270 is of sufficient length to penetrate through the wall of the body duct B before the elongate member or drive tube 260 enters the curved portion of first channel 240.

Figure 12:
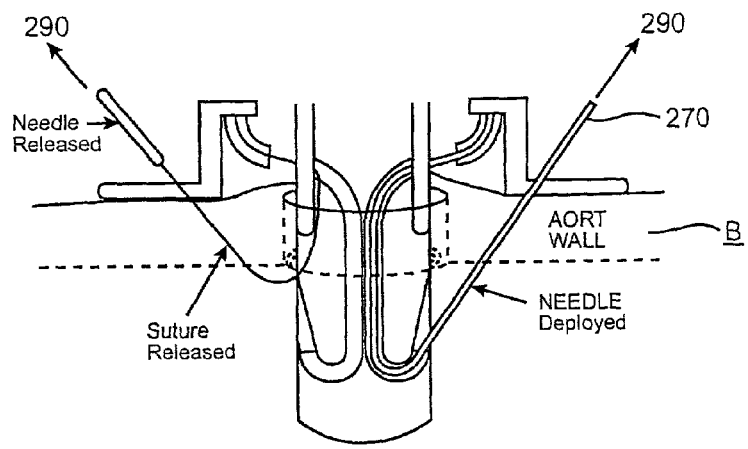
Figures 13, 14:
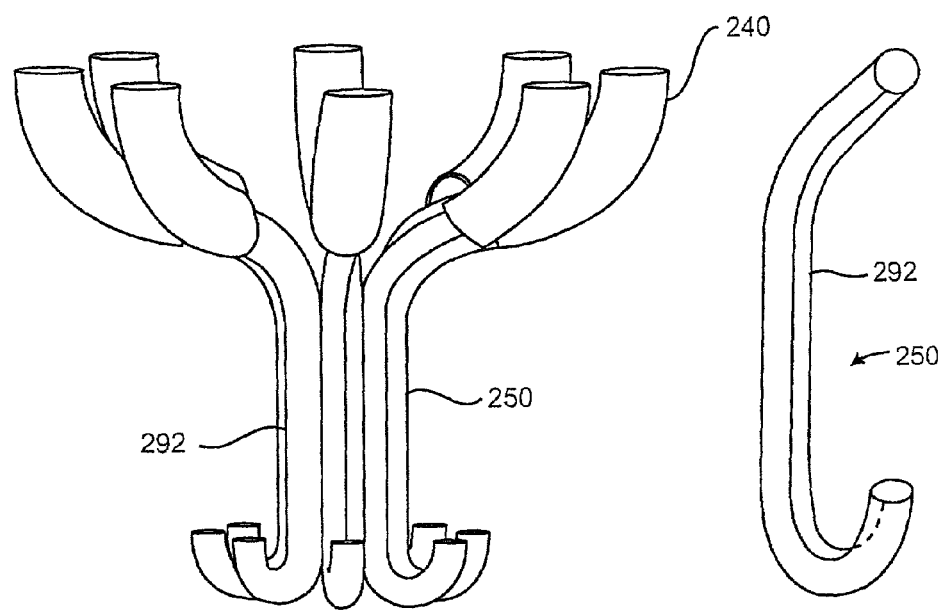
FIGS. 13–14 show the various hypotubes used to guide needles used in the device of FIG. 8.

As shown in FIG. 12, once the needle 270 has penetrated through the wall of the targeted body duct B, the needle 270 is completely removed from the suture device 200 as indicated by arrow 290 and the sutures released from the J-shaped channels 250. Release of the sutures from the second portion 250 of the guide channel allows for the removal of the device 200 once the needles have established a suture path such as that shown in FIG. 1B. As more clearly shown in FIG. 13, each J-shaped channel 250 preferably has a longitudinal slot 292 extending along the entire length of the J-shaped channel. This creates a tube having a C-shaped cross-section as shown in FIG. 14. The slot 292 is of sufficient size to allow for suture removal, but is not of sufficient size to allow a needle 270 to be removed through the slot 292. For example in one embodiment, the slot 292 is about 0.006 inches wide, the channel 250 has an inside diameter of about 0.013 inches, and the needle 270 has a diameter of about 0.010 inches. Once the device 200 has been removed, the sutures 272 may be knotted to complete the anastomosis. The guide channels 240 and 250 and tube 260 may be made of stainless steal hypotube, but it should be understood that other materials, such as various hardened polymers, may also be used as desired. It should be understood that the needles are typically advanced until the distal sharpened tip can be visually observed breaking through the wall of a body duct B such as the aorta. It should also be understood that the device 200 may also be mounted on a pistol grip in a manner similar to that shown for a suture device 10 of FIG. 2.

Figure 15:
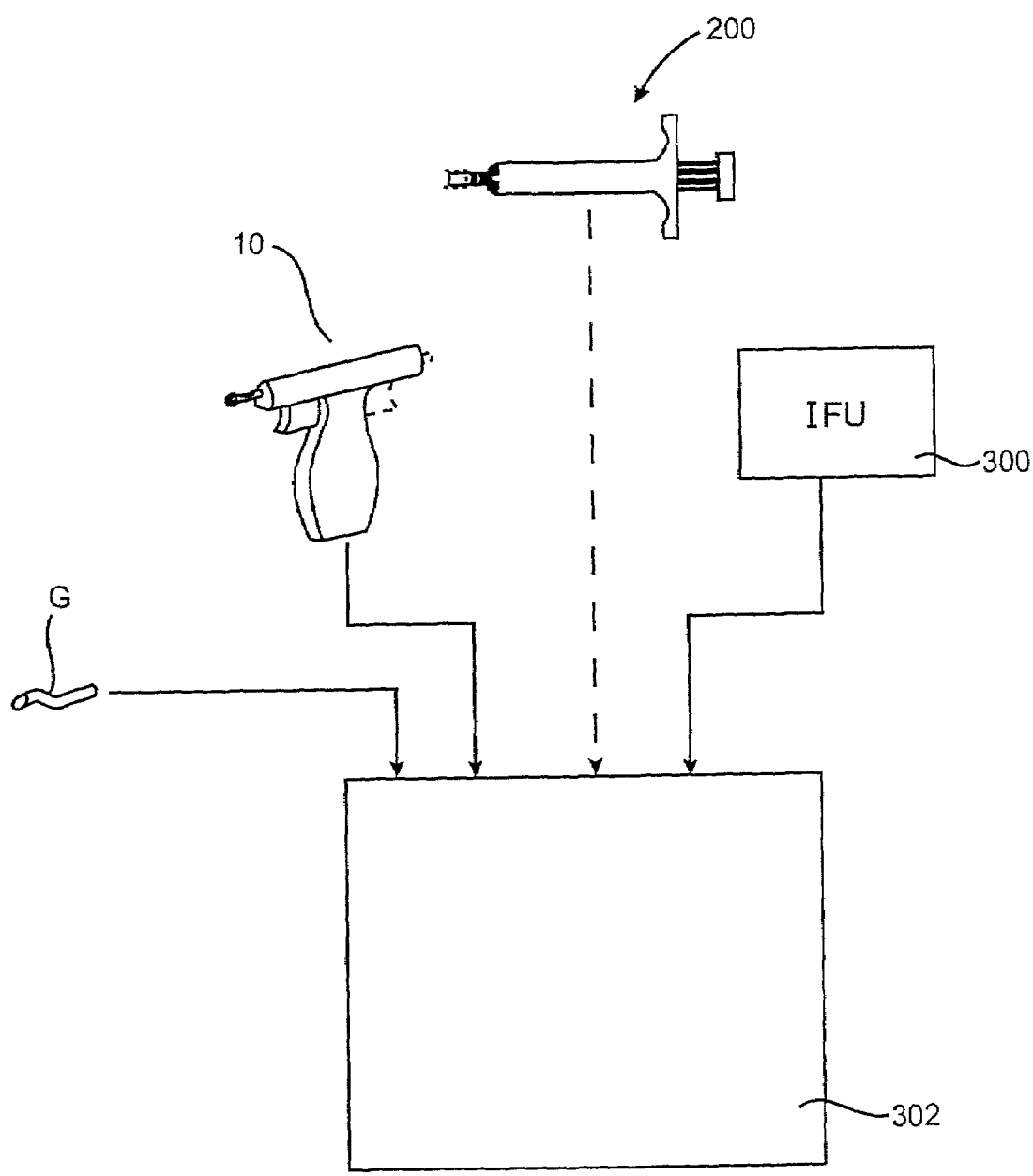
FIG. 15 shows a kit according to the present invention.

Referring now to FIG. 15, the suturing device 10 of the present invention will usually be packaged in kits. In addition to the suturing device 10, such kits will include at least instructions for use 300 (IFU). The suturing device and instructions for use will usually be packaged together within a single enclosure, such as a pouch, tray, box, tube, or the like 302. In alternative embodiments, the kit may include a suturing device 200 in place of the suturing device 10. Some kits may also include the graft G to be sutured to a target vessel. Such grafts G are typically artificial or synthetic. At least some of the components may be sterilized within the container. Instructions for use 300 will set forth any of the methods described above.

While all the above is a complete description of the preferred embodiments of the inventions, various alternatives, modifications, and equivalents may be used. For example, other embodiments of the present invention may have fewer or additional numbers of needles mounted on the distal tip of the suturing device. The needles 30 may have a releasable connection with the inner tube 40. The device may also have other suturing mechanisms such as other end-to-side or side-to-side suturing devices attached to the same pistol grip mounting device to facilitate attachment of a distal end of the graft body duct. The size of the guide tubes used with the needles may be adjusted based on the size/diameter of the needle used. The suturing device may also be equipped with structure to maintain perfusion in the targeted blood vessel. In further alternative embodiments, the suturing device may pass the needle through the targeted body duct first and then through the graft body duct by reversing the direction shown in FIG. 2. Such a device would have a needle drive which delivers its needle through the tissue of the targeted body duct and then into opening 251 to travel up through the J-shaped tube.

Although the foregoing invention has been described in detail for purposes of clarity of understanding, it will be obvious that certain modifications may be practiced within the scope of the appended claims.

What is claimed is:

1. A device for suturing an end of a first body duct to a hole in the side of a second body duct, said device comprising:
a shaft for holding the end of the first body duct and positioning said end adjacent to the hole in the side of the second body duct; and
a plurality of needles arranged on the shaft to be advanced alone a plurality of paths, wherein the shaft has a tubular surface against which the needles are positioned to guide said needles along said path, each path being configured to pass radially into and forwardly out of the end of the first body duct and into the hole of the second body duct and then everts so that the needles will pass outwardly through tissue peripheral to the hole when the end of the first body duct is on the shaft adjacent to the hole in the second body duct.

2. A device as in claim 1, wherein the shaft further comprises a plunger for advancing said needles through the first body duct.

3. A device as in claim 2, wherein the plunger includes suture storage for a plurality of sutures each coupled to one of said plurality of needles.

4. A device as in claim 2, wherein the plunger comprises a plurality of elongate members for advancing said needles through the first body duct.

5. A device as in claim 4, wherein the elongate members comprise tubes each containing a suture coupled to one of said needles.

6. A device as in claim 1, wherein the shaft comprises a plurality of guide channels which define said plurality of paths.

7. A device as in claim 6, wherein the guide channels are arranged in a radial configuration about the shaft.

8. A device as in claim 6, wherein the guide channels comprise guide tubes.

9. A device as in claim 6, wherein the guide channels have a longitudinal slot along a length of at least of one said guide channels.

10. A device as in claim 6, wherein the guide channels each have a first portion and a second portion, wherein the first and second portions are separated by a gap configured to receive the end of the first body duct.

11. A device as in claim 10, wherein the second portion of the guide channel comprises a guide tube having a J-shaped section for guiding one of said needles along a portion of said path.

12. A device as in claim 11, wherein the second portion of the guide channel tube has a longitudinal slot extending along the length of the guide tube having a j-shaped section.

13. A device as in claim 10, wherein: the first portion of the guide channel is adapted to be positioned outside the first body duct and has a distal opening positioned to open towards an outer surface of the first body duct when the first body duct is mounted on the shaft; and the second portion of the guide channel is adapted to be positioned within a lumen of the first body duct when the first body duct is mounted on the shaft, said second portion of the guide channel receiving one of said needles advanced from the first portion and passing through a body duct wall.

14. A device as in claim 13, wherein the second portion of the guide channel has a j-shaped configuration.

15. A device as in claim 13, wherein the second portion of the guide channel includes a longitudinal slot extending the length of the second portion.

16. A device as in claim 13, wherein the needles are of sufficient length to extend from the first portion of the guide channel, through the second portion, and through a tissue layer of the second body duct.

17. A device as in claim 6, wherein at least one of said guide channels has a substantially curved configuration so that one of said needles passing through said guide channel will evert to pass outwardly through tissue peripheral to the hole when the end of the first body duct is on the shaft adjacent to the hole in the second body duct.

18. A device as in claim 1, wherein said needles comprise a shape-memory alloy.

19. A device as in claim 1, wherein said needles comprise a superelastic material.

20. A device as in claim 1, wherein: said needles each have an arcuate profile when unconstrained; said structure comprises a tubular constraint having a lumen surface, wherein the needles are movable between a first position within the tubular constraint where said needles have a substantially straight configuration and a second position within the constraint wherein said needles extend beyond the tubular constraint and assume said arcuate profile.

21. A device as in 20, wherein said tubular constraint comprises an inner tube coaxially mounted with an outer tube, said needles mounted on the distal end of the inner tube wherein said inner tube is movable between a first and second position with the outer tube.

22. A device as in claim 1, wherein the shaft comprises: an outer tube having a passage; and an inner tube slidably mounted in the passage of the outer tube and having the needles fixedly secured to a distal end thereof, said needles adapted to penetrate one end of the first body duct when the body duct is mounted within said inner tube.

23. A device as in claim 22, wherein: said needles each have an arcuate profile when unconstrained; said inner tube is movable between a first position within the outer tube where said needles have a substantially straight configuration and a second position within the outer tube wherein said needles extend beyond the outer tube and assume said arcuate profile.

24. A device as in claim 22, wherein the inner tube has an opening in a wall of the inner tube spaced apart from a distal end of the inner tube, said opening allowing for the insertion of the first body duct into a lumen of the inner tube.

25. A device as in claim 22, wherein the inner tube is coupled to a plunger which reciprocates said inner tube between a forwardly advanced position and a retraifled position.

26. A device as in claim 22, wherein the outer tube and inner tube are in coaxial alignment and have a slideable relationship relative to each other.

27. A device as in claim 22, wherein each of said needles has a suture attached to the distal end of said needles.

28. A device as in claim 22, wherein the needles have arcuate shape memory so that they evert as they are advanced forward.

29. A device as in claim 28, wherein the needles have a sharpened tip pointing proximally when the needles are in a substantially curved configuration.

30. A device as in claim 28, wherein said needles comprise a shape memory material.

31. A device as in claim 22, wherein the needles in said second position has a length sufficient to extend from the inner tube through a wall of the second body duct such that a sharpened tip of the needle penetrates completely through said wall.

32. A device as in claim 22, wherein the needles have a releasable connection with said inner tube.

33. A device as in claim 1, further comprising means for guiding said needles through the first and second body ducts.

34. A device as in claim 33, wherein the means for guiding the needles comprises a plurality of guide channels.

35. A device as in claim 33, wherein the means for guiding the needles comprises a plurality of needles having an arcuate profile when unconstrained and mounted within a tubular constraint, said needles movable between a first position where the tubular constraint forces the needles to a substantially straight configuration and a second position wherein the needle assumes a configuration exhibiting said arcuate profile.

* * * * *